US004001732B2

United States Statutory Invention Registration [19]

[11] Reg. Number: H1732

Johnson

[45] Published: Jun. 2, 1998

[54] ABSORBENT ARTICLES CONTAINING ANTIBACTERIAL AGENTS IN THE TOPSHEET FOR ODOR CONTROL

[76] Inventor: Theresa Louise Johnson, The Procter & Gamble Company, 11050 York Rd., Hunt Valley, Md. 21030-2098

[21] Appl. No.: 212,441

[22] Filed: Mar. 10, 1994

[51] Int. Cl.[6] ..... B32B 1/64

[52] U.S. Cl. ..... 428/68; 428/40; 428/131; 428/245; 428/323; 428/409; 428/905; 604/359; 604/360

[58] Field of Search ..... 428/68, 40, 131, 428/245, 323, 409, 905; 604/359, 360

[56] References Cited

U.S. PATENT DOCUMENTS

| | | | |
|---|---|---|---|
| 2,690,415 | 9/1954 | Shuler | 167/84 |
| 3,093,546 | 6/1963 | Atkinson | 128/290 |
| 3,308,488 | 3/1967 | Schoonman | 5/335 |
| 3,732,867 | 5/1973 | Money | 128/290 R |
| 3,804,094 | 4/1974 | Manoussos et al. | 128/290 R |
| 3,964,486 | 6/1976 | Blaney | 128/284 |
| 4,342,314 | 8/1982 | Radel et al. | 128/287 |
| 4,385,632 | 5/1983 | Odelhog | 604/360 |
| 4,525,410 | 6/1985 | Hagiwara et al. | 428/198 |
| 4,661,101 | 4/1987 | Sustmann | 604/360 |
| 4,795,482 | 1/1989 | Gioffre et al. | 55/75 |
| 4,826,497 | 5/1989 | Marcus et al. | 604/359 |
| 4,911,899 | 3/1990 | Hagiwara | 604/360 |
| 5,019,062 | 5/1991 | Ryan | 428/137 |
| 5,037,412 | 8/1991 | Tanzer et al. | 604/359 |
| 5,122,407 | 6/1992 | Yeo | 428/138 |
| 5,306,487 | 4/1994 | Karapasha | 604/359 |
| 5,342,333 | 8/1994 | Tanzer et al. | 604/359 |

FOREIGN PATENT DOCUMENTS

| | | |
|---|---|---|
| 815446 | 5/1974 | Belgium . |
| 0347746 A1 | 12/1989 | European Pat. Off. . |
| 0389015 A2 | 9/1990 | European Pat. Off. . |
| 0389023 A2 | 9/1990 | European Pat. Off. . |
| 55-38358 | 3/1980 | Japan . |
| 55-38855 | 3/1980 | Japan . |
| 64-15049 | 1/1989 | Japan . |
| WO 93/16670 | 9/1993 | WIPO . |

OTHER PUBLICATIONS

U.S. application No. 07/478,801, Karapasha et al., filed Feb. 12, 1990.

*Primary Examiner*—Charles T. Jordan
*Assistant Examiner*—Meena Chelliah

[57] ABSTRACT

The present invention provides an article of manufacture which minimizes odor caused by bodily fluids, i.e. perspiration, comprising: a liquid pervious topsheet; a liquid impervious backsheet; an absorbent core positioned between the topsheet and the backsheet; and optionally, a means for supporting the article in an appropriate position to perform its absorbency and odor control function; wherein the topsheet comprises an apertured plastic film containing an effective amount of zeolite impregnated with a heavy metal ion; The articles of the present invention provide an increase in the topsheet surface area available for contact with external body fluids such as perspiration, places the antibacterial active in the closest proximity to the skin of the wearer, the active reducing the perspiration malodor by minimizing its formation.

25 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ABSORBENT ARTICLES CONTAINING ANTIBACTERIAL AGENTS IN THE TOPSHEET FOR ODOR CONTROL

TECHNICAL FIELD

The present invention relates to the incorporation of zeolite, impregnated with a heavy metal, into an apertured plastic film topsheet of catamenials to provide an improvement in odor control, i.e., a decrease in perspiration odor by preventing malodor formation. By placing the antibacterial agent in the apertured topsheet, the antibacterial agent is in the closest proximity possible to the perspiration produced on the skin of the wearer.

BACKGROUND OF THE INVENTION

A wide variety of fluid absorbent structures known in the art absorb body fluids such as blood, urine, menses, and the like, and are sanitary and comfortable in use. Disposable products of this type generally comprise fluid-permeable topsheet material, fluid absorbent core, and fluid-impermeable backsheet material. Various shapes, sizes and thicknesses of such articles have been explored in an attempt to make their use more comfortable and convenient.

Odor control in sanitary products has been under investigation for many years. Many body fluids have an unpleasant odor, or develop such odors when in contact with air and/or bacteria for prolonged periods.

Multi-active articles are known in the art and allegedly provide superior odor reduction. Often, the multi-active systems do not eliminate perspiration odors.

Various odor-controlling agents have been disclosed in the literature.

U.S. Pat. No. 2,690,415, Shuler, issued Sep. 28, 1954, teaches particles of odor-absorbing materials uniformly affixed at the interstices of a permeable web by adhesive to provide an odor absorbent medium for, e.g., catamenials.

Particulate carbon, silica gel and activated alumina are noted.

Shifting/displacement of the particulates is assertedly avoided and the sheet is flexible.

ABSCENTS (odor-control molecular sieve from Union Carbide) for use in diapers and catamenials are specifically noted in Union Carbide brochure (A. J. Gioffre 1988). The brochure indicates that UC's market research shows potential benefits in such products. U.S. Pat. Nos. 4,795,482 and 4,826,497, relate to ABSCENTS used as an odor-controlling agent, generally, and in sanitary products, in particular.

Although zeolite, carbon, etc., materials, effectively control many odors associated with body fluids, they do not provide optimal control for perspiration odor. In addition, perspiration often remains on the top of the pad. Therefore, by placing the antibacterial active in the topsheet, the present invention provides placement of the active in close proximity to the perspiration itself.

Apertured topsheets provide various benefits such as quick passage of the discharged fluids through the topsheet and into the absorbent core. Also these topsheets, which do not themselves, absorb fluids, and which are designed to prevent rewet caused by passage of fluid back through the topsheet, provide a more sanitary surface and enhance consumer comfort. Lastly, apertured topsheets provide increased surface area available for external body fluids to come into contact.

Therefore, the object of the present invention is to provide an article of manufacture, i.e. a panty liner and/or a sanitary napkin, wherein the topsheet provides improved perspiration odor control by placing the active in close proximity to the skin of the wearer and by increasing in the surface area of the topsheet for contact with the odoriferous materials.

SUMMARY OF THE INVENTION

Accordingly, the present invention provides an article of manufacture which minimizes odor caused by bodily fluids, i.e., perspiration, comprising:

A. a liquid pervious topsheet;

B. a liquid impervious backsheet;

C. an absorbent core positioned between the topsheet and the backsheet; and

D. optionally, a means for supporting the article in an appropriate position to perform its absorbency and odor control function; wherein the topsheet comprises an apertured plastic film containing an effective amount of zeolite impregnated with a heavy metal ion; preferably the apertured plastic film is selected from the group consisting of apertured formed thermoplastic film, apertured hydroformed thermoplastic film, reticulated thermoplastic film, a thermoplastic scrim, and mixtures thereof; more preferably the topsheet comprises a resilient three-dimensional web exhibiting a fiber-like appearance and tactile impression and comprised of fluid-impervious plastic material, said web having first and second surfaces, the first surface having a multiplicity of apertures therein, each of the apertures being defined by a multiplicity of intersecting fiber-like elements interconnected to one another in the plane of the first surface, each of the fiber-like elements further exhibiting a substantially uniform U-shaped cross-section along its length, the cross-section comprising a base portion in the plane of the first surface and a side wall portion joined to each edge of the base portion, the sidewall portions extending generally in the direction of the second surface of the web, the intersecting sidewall portions being interconnected to one another intermediate the first and the second surfaces of the web, the interconnected sidewall portions terminating substantially concurrently with one another in the plane of the second surface. Preferably the zeolite impregnated with a heavy metal ion is evenly distributed throughout the topsheet material.

The articles of the present invention provide an increase in the topsheet surface area available for contact with external body fluids such as perspiration, places the antibacterial active in the closest proximity to the skin of the wearer, the active reducing the perspiration malodor by minimizing its formation.

BRIEF DESCRIPTION OF THE DRAWINGS

While the specification concludes with claims particularly pointing out and distinctly claiming the present invention, the following description will further illustrate the present invention.

DETAILED DESCRIPTION OF THE INVENTION

Figure 1:
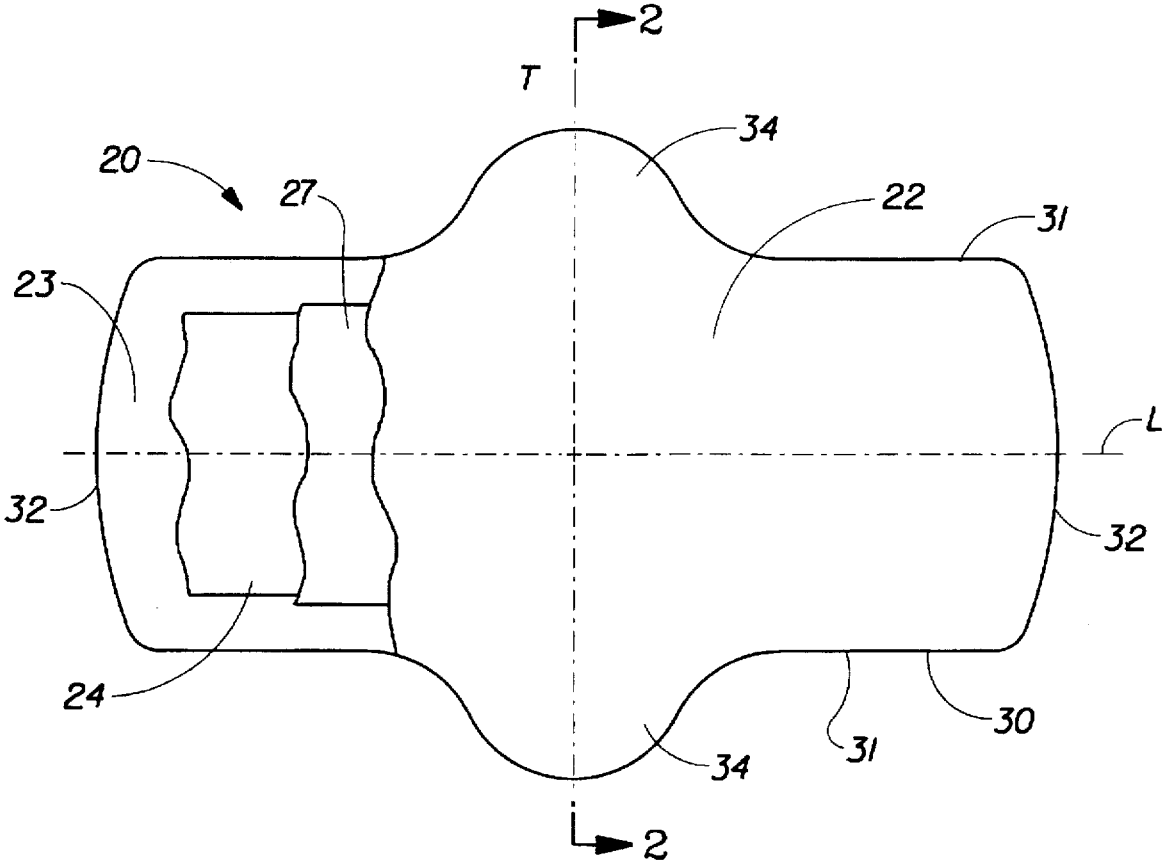
FIG. 1 is a plain view of an absorbent article of the present invention in its flat-out state containing a body contacting apertured topsheet containing an antibacterial agent with portions of the sanitary napkin being cut away.

The present invention relates to an article of manufacturer which minimizes odor caused by bodily fluids, i.e., perspiration, comprising;

A. a liquid pervious topsheet;

B. a liquid impervious backsheet;

C. an absorbent core positioned between the topsheet and the backsheet; and

D. optionally, a means for supporting the article in an appropriate position to perform its absorbency and odor control function; wherein the topsheet comprises an apertured plastic film containing an effective amount, preferably from about 0.05% to about 4%, more preferably from about 0.5% to about 2% of zeolite impregnated with a heavy metal ion; preferably the apertured plastic film is selected from the group consisting of apertured formed thermoplastic film, apertured hydroformed thermoplastic film, reticulated thermoplastic film, a thermoplastic scrim and mixtures thereof; more preferably the topsheet comprises a resilient three-dimensional web exhibiting a fiber-like appearance and tactile impression and comprised of fluid-impervious plastic material, said web having first and second surfaces, the first surface having a multiplicity of apertures therein, each of the apertures being defined by a multiplicity of intersecting fiber-like elements interconnected to one another in the plane of the first surface, each of the fiber-like elements further exhibiting a substantially uniform U-shaped cross-section along its length, the cross-section comprising a base portion in the plane of the first surface and a side wall portion joined to each edge of the base portion, the sidewall portions extending generally in the direction of the second surface of the web, the intersecting sidewall portions being interconnected to one another intermediate the first and the second surfaces of the web, the interconnected sidewall portions terminating substantially concurrently with one another in the plane of the second surface.

Preferably the metal ion is selected from the group consisting of silver, zinc, copper, and mixtures thereof. Topsheet zeolites are selected from the group consisting of A-type zeolite ($SiO_2/Al_2O_3$=1.4 to 2.4), X-type zeolite ($SiO_2/Al_2O_3$=2 to 3), Y-type zeolite ($SiO_2/Al_2O_3$=3 to 6), and mixtures thereof. Preferred zeolites are synthetic A-type zeolites, X-type zeolites, and mixtures thereof.

The zeolite carrier in the topsheet of the articles of the present invention, comprises an aluminate/ silicate framework, with associated actions, M, providing overall electrical neutrality. Empirically, the zeolite framework can be represented as $$x\ AlO_2 .\ y\ SiO_2$$

and the electrically neutral zeolite as $$x/n\ M .\ x\ AlO_2 .\ y\ SiO_2 .\ z\ H_2O$$

wherein: x and y are each integers, M is a ion-exchangeable metal ion, which is usually the ion of a monovalent or divalent metal and n is the valence of the metal. As noted by the empirical formula, zeolites may also comprise waters of hydration (z $H_2O$).

Topsheet zeolites are selected from the group consisting of A-type zeolite ($SiO_2/Al_2O_3$=1.4 to 2.4);, X-type zeolite ($SiO_2/Al_2O_3$=2 to 3), Y-type zeolite ($SiO_2/Al_2O_3$=3 to 6), and mixtures thereof. Preferred zeolites are synthetic A-type zeolites, X-type zeolites, and mixtures thereof.

In addition to the above sources of zeolites, polyethylene (low density) film containing about 2% of a silver/zinc mixture is available from Kanebo U.S.A. under the tradename LDPE Bactikiller® AZ Film.

Optionally, the absorbent core of the articles of the present invention comprise an effective amount of an adjunct odor-controlling agent, preferably from about 0.01 g to about 15 g per article, more preferably from about 0.1 g to about 10.0 g per article, the adjunct odor controlling agent selected from the group consisting of:

a. zeolite;

b. activated carbon;

c. silica gel;

d. moisture activated encapsulated perfume;

e. cyclodextrin;

f. activated alumina; and g. mixtures thereof.

Articles of the present invention can be made by constituents which are well known in the art. Also, methods and apparatus for assembling catamenials are also known in the art. Not intending to be limiting, the following exemplifies the articles of the present invention.

As used herein, the term "absorbent article" refers to devices which absorb and contain body exudates, and, more specifically, refers to devices which are placed against or in proximity to the body of the wearer to absorb and contain the various exudates discharged from the body. A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

FIG. 1 is a plan view of the sanitary napkin 20 of the present invention in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a liquid pervious topsheet 22, a liquid impervious backsheet 23 joined with the topsheet 22, an absorbent core 24 and secondary topsheet 27 positioned between the topsheet 22 and the backsheet 23.

The sanitary napkin 20 has two surfaces, a body-contacting surface or "body surface" **20*a* and a garment surface 20*b*. The sanitary napkin 20 is shown in FIG. 1 as viewed from its body surface 20*a*. The body surface 20*a* is intended to be worn adjacent to the body of the wearer while the garment surface 20*b* is on the opposite side and is intended to be placed adjacent to the wearer's undergarments when the sanitary napkin 20 is worn. The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction. FIG. 1 also shows that the sanitary napkin 20 has a periphery 30, which is defined by the outer edges of the sanitary napkin 20 in which the longitudinal edges are designated 31 and the end edges are designated 32**.

While the topsheet, the backsheet, and the absorbent core may be assembled in a variety of well known configurations (including so called "tube" products or side flap products), preferred sanitary napkin configurations are described generally in U.S. Pat. No. 4,950,264, "Thin, Flexible Sanitary Napkin," Osborn, issued on Aug. 21, 1990; U.S. Pat. No. 4,425,130, "Compound Sanitary Napkin," DesMarais, issued on Jan. 10, 1984; U.S. Pat. No. 4,321,924, "Bordered Disposable Absorbent Article," Ahr, issued on Mar. 30, 1982; U.S. Pat. No. 4,589,876, "Shaped Sanitary Napkin With Flaps", Van Tilburg, issued on Aug. 18, 1987. Each of these patents are incorporated herein by reference.

FIG. 1 shows a preferred embodiment of the sanitary napkin 20 in which the topsheet 22 and the backsheet 23 have length and width dimensions generally larger than those of the absorbent core 24. The topsheet 22 and the backsheet 23 extend beyond the edges of the absorbent core 24 to thereby form not only portions of the periphery but also side flaps or wings 34.

Figure 2:
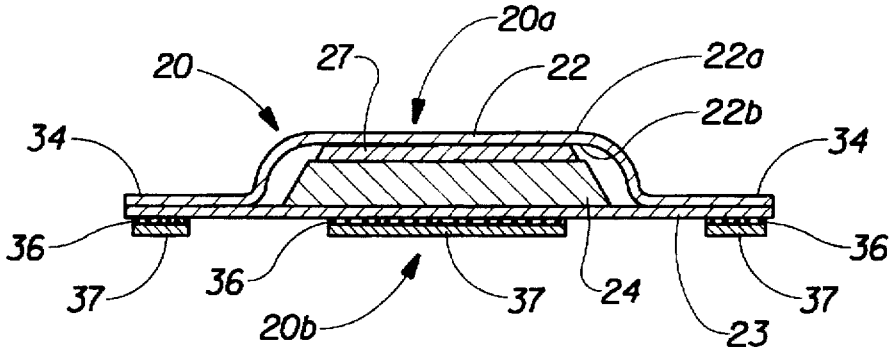
FIG. 2 is a cross-sectional view of an absorbent article comprising an apertured topsheet containing an antibacterial agent.

FIG. 2 is a cross-sectional view of the sanitary napkin 20 taken along section line 2—2 of FIG. 1. FIG. 2 shows the secondary topsheet 27, just below the topsheet 22. The wing 34 is an extension of the topsheet 22. The fastening means 36 together with the release liner 37 maintains the article in place so that it can perform its intended function.

Figure 3:
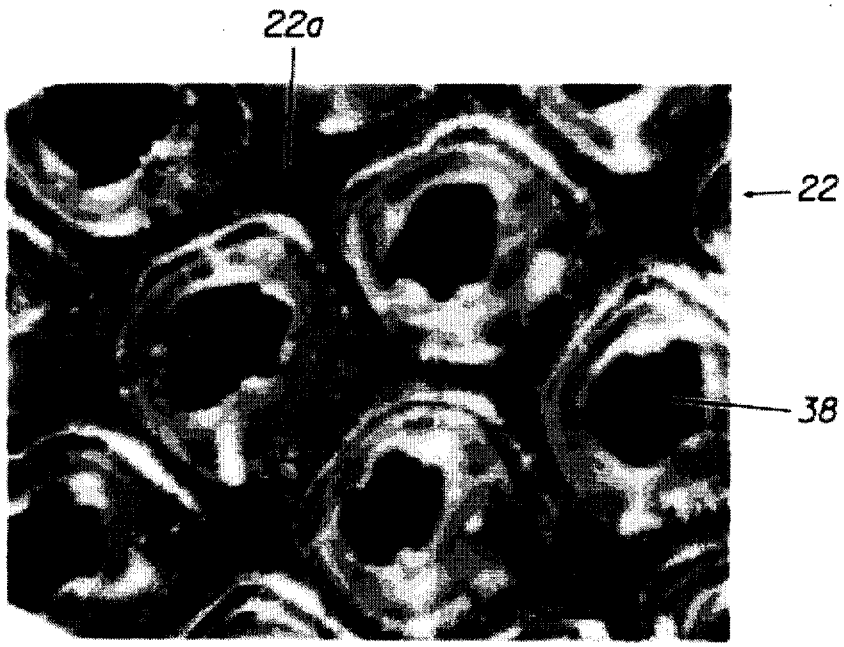
FIG. 3 is a greatly enlarged photograph of a segment of a three-dimensional topsheet of the type generally illustrated in FIGS. 1 and 2.

FIG. 3 is a plan view photograph enlarged approximately 27 times actual size of a preferred embodiment of a three-dimensional, fiber-like, fluid-pervious plastic topsheet 22 of the present invention. As can be seen in the enlarged photograph of FIG. 3, the web's fiber-like appearance is comprised of a continuum of fiber-like elements, each end of the fiber-like elements being interconnected to at least one other of said fiber-like elements. The fiber-like plastic topsheet 22 is particularly well suited for use as a topsheet in a sanitary napkin of the type generally illustrated in FIG. 1. FIG. 3 is an illustration of the body surface **22*a* of the topsheet 22. The topsheet 22, which exhibits a fiber-like appearance, embodies a three-dimensional microstructure comprising a regulated continuum of capillary networks of steadily decreasing size extending from the uppermost or body surface 22*a* to the lowermost or garment surface 22*b* thereof to promote rapid liquid transport from the surface 22*a* to the garment facing surface 22*b*** surface of the topsheet without lateral transmission of said liquid between adjacent capillary networks.

A typical capillary network of the type generally shown in FIG. 3 comprises an uppermost capillary opening 38 formed by a multiplicity of primary fiber-like elements, i.e. elements.

The topsheet 22 is compliant, soft feeling, and non-irritating to the wearer's skin. Further, the topsheet 22 is liquid pervious permitting liquids (e.g., menses and/or urine) to readily penetrate through its thickness. A suitable topsheet 22 is manufactured from materials such as apertured formed thermoplastic films, apertured plastic films, apertured hydroformed thermoplastic films; reticulated thermoplastic films; and thermoplastic scrims. The topsheets of the present invention are described in detail in U.S. Pat. No. 4,342,314 entitled "Resilient Plastic Web Exhibiting Fiber-Like Properties," Radel et al., issued on Aug. 3, 1982, which is herein incorporated by reference, especially column 4, line 41 to column 6, line 44. Preferred methods of making the topsheets of the present invention are disclosed in U.S. Pat. No. 4,637,819, Ouellette et al., issued on Jan. 20, 1987 and U.S. Pat. No. 4,839,216, Curro et al., issued Jun. 13, 1989, which are herein incorporated by reference.

The apertured topsheets of the present invention are pervious to body exudates and yet non-absorbent and have a reduced tendency to allow liquids to pass back through and rewet the wearer's skin. Thus, the surface of the apertured topsheet which is in contact with the body remains dry, thereby reducing body soiling and creating a more comfortable feel for the wearer.

Other formed films are described in U.S. Pat. No. 3,929,135, entitled "Absorptive Structures Having Tapered Capillaries," Thompson, which issued on Dec. 30, 1975; U.S. Pat. No. 4,324,246 entitled "Disposable Absorbent Article Having A Stain Resistant Topsheet", Mullane, et al., issued on Apr. 13, 1982; U.S. Pat. No. 4,463,045 entitled "Macroscopically Expanded Three-Dimensional Plastic Web Exhibiting Non-Glossy Visible Surface and Cloth-Like Tactile Impression", Ahr et al., issued on Jul. 31, 1984; and U.S. Pat. No. 5,006,394 "Multilayer Polymeric Film", Baird, issued on Apr. 9, 1991. Each of these patents are incorporated herein by reference. Other preferred topsheets for the present invention are the formed film described in one or more of the above patents and marketed on sanitary napkins by The Procter & Gamble Company of Cincinnati, Ohio as "DRI-WEAVE".

In a preferred embodiment of the present invention, the body surface of the topsheet is hydrophilic so as to help liquid to transfer through the topsheet faster than if the body surface was not hydrophilic. This will diminish the likelihood that menstrual fluid and perspiration will flow off the topsheet rather than flowing into and being absorbed by the absorbent core. In a preferred embodiment, surfactant is incorporated into the polymeric materials of the formed film topsheet such as is described in U.S. patent application Ser. No. 08/072,660 filed Jun. 4, 1993, incorporated herein by reference, which is a continuation of U.S. patent application Ser. No. 07/794,745, "Absorbent Article Having A Nonwoven and Apertured Film Coversheet," Aziz, et al., filed on Nov. 19, 1991, now abandoned.

Alternatively, the body surface of the topsheet can be made hydrophilic by treating it with a surfactant such as is described in the above referenced U.S. Pat. No. 4,950,254, incorporated herein by reference.

The absorbent core 24 may be any absorbent means which is capable of absorbing or retaining liquids (e.g., menses and/or urine). The absorbent core 24 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones) (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,950,264 entitled "Thin, Flexible Sanitary Napkin" issued to Osborn on Aug. 21, 1990 which is incorporated herein by reference. A preferred embodiment of the absorbent core of the present invention optionally comprises an effective amount of an adjunct odor-controlling agent, preferably from about 0.01 g to about 15 g per article, more preferably from about 0.1 g to about 10.0 g per article, the odor controlling agent selected from the group consisting of:

a. zeolite;

b. activated carbon;

c. silica gel;

d. moisture activated encapsulated perfume;

e. cyclodextrin;

f. activated alumina; and g. mixtures thereof.

The backsheet 23 and the topsheet 22 are positioned adjacent the garment facing surface and the body facing surface, respectively, of the absorbent core 24 and are preferably joined thereto and to each other by attachment means (not shown) such as those well known in the art. For example, the backsheet 23 and/or the topsheet 22 may be secured to the absorbent core 24 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, OH, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23.

In use, the sanitary napkin 20 can be held in place by any support means, fastening means, or attachment means **3*b* well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697 incorporated herein by reference. Before the sanitary napkin is placed in use, the pressure-sensitive adhesive is typically covered with a removable release liner 37 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The sanitary napkin 20** of the present invention is used by removing the release liner and thereafter placing the sanitary napkin in a panty so that the adhesive contacts the panty. The adhesive maintains the sanitary napkin in its position within the panty during use.

In a preferred embodiment of the present invention, the sanitary napkin has two flaps 34 each of which are adjacent to and extend laterally from the side edge of the absorbent core. The flaps are configured to drape over the edges of the wearer's panties in the crotch region so that the flaps are disposed between the edges of the wearer's panties and the thighs. The flaps serve three purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. Lastly, articles with flaps have increased surface area of the topsheet so that potentially a greater amount of zeolite impregnated with a heavy metal ion will come into contact with odoriferous material, i.e. perspiration.

The flaps can be constructed of various materials including materials similar to the topsheet, backsheet, tissue, or combination of these materials, but preferably is constructed of the topsheet materials. When these flaps are constructed of the apertured film topsheet of the present invention, then the zeolite impregnated with heavy metal ions, can be incorporated into the top layer of the flaps. Further, the flaps may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986, all of which are incorporated herein by reference.

In a preferred embodiment of the present invention, an acquisition layer(s) 27 may be positioned between the topsheet and the absorbent core. The acquisition layer 27 may serve several functions including improving wicking of exudates over and into the absorbent core. There are several reasons why the improved wicking of exudates is important, including providing a more even distribution of the exudates throughout the absorbent core and allowing the sanitary napkin 20 to be made relatively thin. (The wicking referred to herein may encompass the transportation of liquids in one, two or all directions (i.e. in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al. All of the above references are incorporated herein by reference.

In a preferred embodiment, the acquisition layer may be joined with the topsheet by any of the conventional means for joining webs together, most preferably by fusion bonds as is more fully described in the above-referenced Cree application.

While particular embodiments of the present invention have been illustrated and described, various other changes and modifications can be made without departing from the spirit and scope of the invention. Therefore the appended claims cover all such changes and modifications that are within the scope of this invention.

Optional Adjunct Odor-Controlling Agents

The articles of this invention can optionally contain an effective, i.e., odor-controlling, amount of an adjunct odor-controlling agent, preferably from about 0.01 g to about 15 g per article, more preferably from about 0.1 g to about 10.0 g per article, the odor controlling agent selected from the group consisting of:

a. zeolite;

b. activated carbon;

c. silica gel;

d. moisture activated encapsulated perfume;

e. cyclodextrin;

f. activated alumina; and g. mixtures thereof.

Zeolites

In general terms, traditional zeolites comprise an aluminate/ silicate framework, with associated actions, M, providing overall electrical neutrality. Empirically, the zeolite framework can be represented as $$x\ AlO_2 .\ y\ SiO_2$$

and the electrically neutral zeolite as $$x/n\ M\ .\ x\ AlO_2 .\ y\ SiO_2 .\ zH_2\ O$$

wherein: x and y are each integers, M is a cation and n is the charge on the cation. As noted by the empirical formula, zeolites may also comprise waters of hydration (z $H_2O$). M can be a wide variety of cations, e.g., $Na^+$, $K^+$, $NH_4^+$, alkylammonium, and the like.

A preferred class of zeolites useful as the optional adjunct odor controlling agent is characterized as "intermediate" silicate/aluminate zeolites. The "intermediate" zeolites are characterized by $SiO_2/AlO_2$ molar ratios of less than about 10. Typically, the molar ratio of $SiO_{2_2}/AlO_{2_2}$ will range from about 2 to about 10. The intermediate zeolites are disclosed in U.S. Pat. Nos. 4,795,482 and 4,826,497, which are incorporated herein by reference. The intermediate zeolites have a larger surface area (about 700–800 $m^2/g$) versus high zeolites (about 400 $m^2/g$). Therefore, less intermediate zeolite may be needed to absorb a given amount of odor, etc., on a weight to weight basis. Also, intermediate zeolites are more moisture tolerant and retain more absorbing capacity in the presence of water.

A wide variety of intermediate zeolites suitable for use herein are commercially available as VALFOR CP301-68, VALFOR 300-63, VALFOR CP300-35, VALFOR CP300-56, and CBV 400 through CBV 760 Series, all from PQ Corporation.

The zeolites used herein are not of the fibrous type, e.g., various Mordenites, and some types of Y zeolites, since these may be subject to safety issues. Accordingly, the term "zeolite" as used herein is intended to encompass only the nonfibrous zeolites. While some naturally-occurring zeolites meet the objectives of this invention, the synthetic zeolites of the types available in commerce are generally more preferred. Synthetic zeolites include A-type zeolite ($SiO_2/Al_2O_3$=1.4 to 2.4), X-type zeolite ($SiO_2/Al_2O_3$=2 to 3), and Y-type zeolite ($SiO_2/Al_2O_3$=3 to 6). Preferred zeolites are synthetic Y-type zeolites.

Even though intermediate zeolites are preferred, high zeolites can be employed as adjunct odor controlling agents in the practice of this invention alone or in combination with the intermediate ratio zeolites. High zeolites include, for example, the well-known "molecular sieve" zeolites of the ZSM, beta zeolite, etc., type (generally in the 1–10 micron particle size range) and the zeolite materials marketed under the trade name ABSCENTS by the Union Carbide Corporation and UOP. ABSCENTS are typically available as a white powder in the 3–5 micron particle size range (See: ABSCENTS, A New Approach for Odor Control by A. J. Gioffre, copyright 1988 by the Union Carbide Corporation).

Various other modified zeolite-type materials which can be used in the present invention, such as the manganese-aluminum-phosphorus-silicon-oxide molecular sieves and other zeolite odor-controlling compositions are described in U.S. Pat. Nos. 4,793,833, Lok et al.; 4,604,110; 4,437,429; and 4,648,977, which are incorporated herein by reference.

Carbon Odor-Controlling Agent

The carbon material employed herein is the material well known in commercial practice as an adsorbent for organic molecules and/or for air purification purposes. Carbon suitable for use herein is available from a variety of commercial sources under trade names such as CALGON Type "CPG", Type "PCB", Type "SGL", Type "CAL", and Type "OL." Often, such carbon material is referred to simply as "activated" carbon or "activated" charcoal. It is to be understood that any of the "air purifying" or "activated" carbons of commerce can be used in the practice of this invention.

If the zeolites herein are optionally used in conjunction with the activated carbon, it is preferred (for aesthetics reasons) to coat the carbon with the zeolite using a binder.

Moisture-Activated Encapsulated Perfume

The compositions and articles of this invention optionally contain an effective amount of various moisture-activated encapsulated perfume particles. Such materials include, for example, cyclodextrin/perfume inclusion complexes, polysaccharide cellular matrix perfume microcapsules, and the like. Encapsulation of perfume minimizes interaction with, and/or depletion by, odor-absorbing materials before use of the product. Perfume is released when the materials are wetted, to provide a pleasant odor signal in use. Especially preferred are cyclodextrin inclusion complexes of volatile perfumes, with a particle size of less than about 12 microns. U.S. patent application Ser. No. 07/707,266, Trinh et. al., filed Mar. 6, 1990, from page 13, line 16 to page 14, line 33, which is herein incorporated by reference, discloses the formation of cyclodextrin/perfume inclusion complexes. A description of appropriate cyclodextrin/perfume complex particle size is also disclosed in '266, page 14, line 34 to page 16, line 12, which is also incorporated herein by reference.

It is essential that at least an effective amount of the cyclodextrin/perfume complex be applied to the article. Effective amounts are typically in the range of from about 0.005 g to about 10 g, preferably from about 0.01 g to about 3 g, more preferably from about 0.02 g to about 1 g per article.

Perfume

The perfumes which can optionally be incorporated into the articles of this invention are the conventional ones known in the art. Selection of any perfume component, or amount of perfume, is based on functional and aesthetic considerations. Preferred perfume components useful in the present invention are highly volatile and moderately volatile perfume ingredients, more preferably the highly volatile, low boiling perfumes.

The highly volatile, low boiling, perfume ingredients typically have boiling points of about 250° C. or lower. These highly volatile perfumes are fleeting and are quickly lost as they are released. Many of the more moderately volatile perfume ingredients are also quickly lost. The moderately volatile perfume ingredients are those having boiling points of from about 250° C. to about 300° C. Many perfume ingredients along with their odor characters, and their physical and chemical properties, such as boiling point and molecular weight, are given in "Perfume and Flavor Chemicals (Aroma Chemicals)," Steffen Arctander, published by the author, 1969, incorporated herein by reference.

Examples of moderately volatile perfume ingredients and highly volatile, low boiling, perfume ingredients are disclosed in U.S. patent application Ser. No. 07/707,266, Trinh et al., filed Mar. 6, 1990, page 8, line 13 to page 9, line 4, which is herein incorporated by reference.

Matrix Perfume Microcapsules

Water-soluble cellular matrix perfume microcapsules are solid particles containing perfume stably held in the cells. The water-soluble matrix material comprises mainly polysaccharide and polyhydroxy compounds. The polysaccharides are preferably higher polysaccharides of the non-sweet, colloidally-soluble types, such as natural gums, e.g., gum arabic, starch derivatives, dextrinized and hydrolyzed starches, and the like. The polyhydroxy compounds are preferably alcohols, plant-type sugars, lactones, monoethers, and acetals. The cellular matrix microcapsules useful in the present invention are prepared by, e.g., (1) forming an aqueous phase of the polysaccharide and polyhydroxy compound in proper proportions, with added emulsifier if necessary or desirable; (2) emulsifying the perfumes in the aqueous phase; and (3) removing moisture while the mass is plastic or flowable, e.g., by spray drying droplets of the emulsion. The matrix materials and process details are disclosed in, e.g., U.S. Pat. No. 3,971,852, Brenner et al., issued Jul. 27, 1976, which is incorporated herein by reference.

The present invention preferably has minimal non-encapsulated surface perfume, preferably less than about 1%.

Moisture-activated perfume microcapsules can be obtained commercially, e.g., as IN-CAPR from Polak's Frutal Works, Inc., Middletown, N.Y. and as Optilok System® encapsulated perfumes from Encapsulated Technology, Inc., Nyack, N.Y.

Water-soluble matrix perfume microcapsules preferably have size of from about 0.5 micron to about 300 microns, more preferably from about 1 micron to about 200 microns, most preferably from about 2 microns to about 100 microns.

It is essential that at least an effective amount of the water-activated matrix perfume microcapsules be applied to the article. Effective amounts are typically in the range of from about 0.001 g to about 5 g, preferably from about 0.005 g to about 1 g, more preferably from about 0.01 g to about 0.5 g, per article.

Incorporation of Encapsulated Perfume into Absorbent Articles

Small particle size cyclodextrin/perfume complexes can be applied to the fluid absorbent articles by uniformly sprinkling, mixing, or distributing the cyclodextrin/perfume complex powder onto the fluid absorbent materials.

However, it is commonly known that when in use, the body fluid is not normally distributed to the whole fluid absorbent article, e.g., sanitary napkin, but usually localized in a portion of the article. Similarly, it is not necessary to apply the cyclodextrin/perfume complex powder to the entire fluid absorbent article. Preferably, cyclodextrin/perfume complex powder is applied to areas most likely to be wetted by body fluids to avoid waste in the areas which do not normally receive the body fluids.

Furthermore, when distributed as a dry powder, the cyclodextrin/perfume complex particles may shift away from the preferred locations, and move to the areas where they have less chance to be solubilized by the body fluids, and become less effective. The shifting happens both during the manufacturing processes, e.g., folding, and packaging of the articles, and during later steps, e.g., transportation, and unfolding and refolding of the fluid absorbent article in use.

Therefore, it is preferred to provide a means to immobilize the cyclodextrin/perfume complex powder on the preferred locations in the fluid absorbent articles.

Immobilization can be accomplished by a variety of methods, i.e., hot-melt adhesives, thermoplastic binder fibers, thermoplastic binder particles, or other methods known to those skilled in the art.

A preferred method is to use a water-soluble binder to attach the cyclodextrin/perfume complex powder to the fluid absorbent core and/or topsheets. The water-soluble binders are preferably polymeric. They can be low melting polymers such as polyethylene glycols (PEG), poly(ethylene glycol) methyl ethers, or mixtures thereof. Preferred low melting water-soluble PEG materials have the general formula RO—($CH_2CH_2$ O)—R wherein each R is a hydrogen radical, a $C_1$–$C_4$ alkyl radical, or mixtures of such radicals, and have an average molecular weight (MW) of from about 600 to about 20,000 (n is from about 13 to about 450). More preferred PEG materials are polyethylene glycols, poly (ethylene glycol) methyl ethers, or mixtures thereof, with MW of from about 1,000 to about 9,000 (n from about 20 to about 200), more preferably from about 1,400 to about 4,500 (n from about 30 to about 100). The weight ratio of the cyclodextrin/perfume complex to the PEG material is from about 3:1 to about 1:5, preferably from about 2:1 to about 1:3.

A preferred process of attaching cyclodextrin/perfume complex powder involves admixing solid small-particle-sized cyclodextrin/perfume complex powder with a molten hydrophilic PEG material. The molten mixture can be sprayed directly to the dry fluid absorbent materials or topsheets, then letting the droplets solidify on said materials or nonwoven topsheets. Another preferred method is to pulverize the solidified cyclodextrin complex/binder mixture into small particles first. Said particles can then be attached and immobilized to the surface of the fluid absorbent materials or the nonwoven topsheets by distributing the particles on said surface, melting said particles by, e.g., a heat source, and then resolidifying to bind said particles to said surface. At the cyclodextrin/perfume complex to the PEG material weight ratio of from about 3:1 to about 1:3, the molten mixture can be solidified to room temperature then pulverized at room temperature or cryogenically. At the cyclodextrin/perfume complex to the PEG material weight ratio of from about 1:2 to about 1:5, the molten mixture can be prilled by, e.g., spray drying, marumarizing, etc., into solid prills. The solid cyclodextrin/perfume complex/PEG material mixture particles preferably have sizes of from about 10 microns to about 1,000 microns, more preferably from about 20 microns to about 600 microns.

Another preferred method is to apply the cyclodextrin/perfume complex slurry to the fluid absorbent material and/or nonwoven topsheet. Upon drying, the small particles of the cyclodextrin complex adhere to the absorbent material and are immobilized on said material. This can be done, e.g., by spraying the cyclodextrin/perfume complex slurry onto the already formed and dry absorbent fiber web.

It is also preferred to incorporate a water-soluble polymer, such as PEG, polyvinyl alcohols, polyacrylic acids, and polyvinylpyrrolidone into the aqueous cyclodextrin/perfume complex slurry after the complex has been formed. The aqueous mixture is distributed, e.g., by spraying, to the fluid absorbent materials or the nonwoven topsheets, then the resulting combination is dried, and thus attaching the cyclodextrin to said fluid absorbent materials or topsheets. Preferred MW of said polymers are from about 1,000 to about 200,000; more preferred are from about 2,000 to about 100,000.

Cyclodextrin

As used herein, the term "cyclodextrin" (uncomplexed) includes any of the known cyclodextrins such as unsubstituted cyclodextrins containing from six to twelve glucose units, especially, alpha-, beta-, and gamma-cyclodextrins, and/or their derivatives, and/or mixtures thereof. A more complete disclosure of uncomplexed cyclodextrins which optionally be used in the articles of the present invention are disclosed in U.S. patent application Ser. No. 08/268,157 filed Jun. 29, 1994, incorporated herein by reference, which is a continuation of pending U.S. patent application Ser. No. 07/707,266, Trinh et al., Supra, page 4, line 12 to page 5, line 26, which is incorporated herein by reference.

All percentages, ratios, and parts herein, in the Specification, Examples, and claims, are by weight and are approximations unless otherwise stated.

The following are non-limiting examples of the present invention.

Example 1

A three-dimensional apertured polymeric web of this invention is made using the process disclosed in U.S. Pat. No. 4,839,216, Curro et al., issued on Jun. 13, 1989, which is herein incorporated by reference.

A web of non-apertured poly(ethylene) film 11 (LDPE Bactekiller AZ® 1% available from Kanebo USA containing about 1% of zeolite impregnated with a heavy metal ion) is fed onto the forming structure at a speed of about 360 feet per minute and is subjected to a high pressure water jet. The forming structure uses a screen having a pattern of shaped apertures. This particular screen has a repeating geometric pattern of non-equilateral pentagon shaped holes 97 of about 0.035 inches in size with the width of metal between the holes of about 0.007 inches. The flow of water from spray nozzles is evenly spaced about 1.25 inches apart and centered across the web of the film. The spray nozzles are type 2540 wash jets available from Spraying System Co., Wheaton, Ill. They provide a flat spray at the angle of about 25 degrees. Water is supplied to the nozzles at a temperature of about 178° F. and at a pressure of about 1150 psig. The nozzles are set such that the spray angle is about 25 degrees parallel to and centered in the cross-machine direction.

The resulting apertured topsheet is dried of residual water by blotting with an absorbent medium or by blowing warm air over or through the sheet.

EXAMPLE 2

A trifold wet-laid tissue containing approximately 5 g of absorbent gelling material per square foot (which yields about 0.68 g absorbent gelling material per sanitary napkin pad at a folded size of 20 cm×7 cm) is used as the core. An additional piece of tissue is positioned on top of the core as a secondary topsheet.

The absorbent structure prepared as above is placed on top of a slightly larger piece of polyethylene backsheet, with the piece of tissue exposed on top. A formed-film topsheet of the type disclosed in Example 1 is coated evenly on its underside with about 0.03 g of a latex adhesive, and excess adhesive is wiped off. The topsheet is rolled with a glass rod to ensure good contact and proper application of adhesive. The topsheet is then placed on top of the above-prepared core assembly. To ensure good topsheet-to-core bonding, the topsheet is weighted with a piece of Plexiglas.

The assembly is sealed together at the edges with a hot iron using a metal mold of the desired shape attached to and heated by the iron. The overall product consists of: Bactekiller® containing topsheet/tissue/absorbent core/backsheet. Optionally, adhesive can be applied on the outside of the backsheet of the pad for affixing the article to undergarments. The topsheet of the product is sprayed with about 0.03 g of Pegosperse 200ML nonionic surfactant (PEG 200) to hydrophilize the fluid-receiving surface of the topsheet.

While the foregoing illustrates the preparation of a sanitary napkin in the manner of this invention, an entirely similar operation can be employed to prepare a pantiliner (generally of the dimensions approximately 14 cm×5 cm) with appropriate modifications of the amount of the ingredients, as noted herein above.

EXAMPLE 3

A trifold wet-laid tissue containing approximately 5 g of absorbent gelling material per square foot (which yields about 0.68 g absorbent gelling material per sanitary napkin pad at a folded size of about 20 cm×7 cm) is used to prepare the core. The trifold tissue laminate is sprayed with fine mist of water and opened to expose the absorbent gelling material. About 0.5 g of Valfor CP300-56 zeolite is sprinkled onto the AGM. The two sides of the tissue are folded back to their original position, thereby sealing the absorbent gelling material and zeolite inside. The still moist core is resealed by using a hot iron, pressing firmly. About 0.2 g of cyclodextrin/perfume poly(ethylene glycol) [PEG] complex is sprinkled onto the dry core, with a higher concentration at the central area of the core surface. An additional piece of tissue is positioned on top of the core as a secondary topsheet. A hot iron is pressed on top of the tissue to melt the PEG of the cyclodextrin/perfume complex so that upon cooling the complex particles are immobilized on the core surface and the tissue.

An absorbent core prepared in the foregoing manner is placed on top of a slightly larger piece of polyethylene backsheet, with the piece of tissue exposed on top. A formed-film topsheet of the type disclosed in Example 1 is coated evenly on its underside with about 0.03 g of a latex adhesive, and excess adhesive is wiped off. The topsheet is rolled with a glass rod to ensure good contact and proper application of adhesive. The topsheet is then placed on top of the above-prepared core assembly. To ensure good topsheet-to-core bonding, the topsheet is weighted with a piece of Plexiglas.

The assembly is sealed together at the edges with a hot iron using a metal mold of the desired shape attached to and heated by the iron. The overall product consists of: Bacte-killer containing topsheet/tissue/cyclodextrin complex/absorbent core with zeolite/backsheet. Optionally, adhesive can be applied on the outside of the backsheet of the pad for affixing the article to undergarments. The topsheet of the product is sprayed with about 0.03 g of Pegosperse 200ML nonionic surfactant (PEG 200) to hydrophilize the fluid-receiving surface of the topsheet.

While the foregoing illustrates the preparation of a sanitary napkin in the manner of this invention, an entirely similar operation can be employed to prepare a pantiliner (generally of the dimensions approximately 14 cm×5 cm) with appropriate modifications of the amount of the ingredients, as noted herein above.

What is claimed is:

1. A disposable absorbent article which minimizes the odor that can be caused by bodily fluids and perspiration, comprising:

A. a liquid pervious topsheet;

B. a liquid impervious backsheet;

C. an absorbent core positioned between the topsheet and the backsheet; and

D. optionally, a means for supporting the article in an appropriate position to perform its absorbency and odor control functions;

wherein the topsheet comprises an apertured plastic film positioned for contacting the wearer's body, the apertured plastic film containing from about 0.05% to about 4% by weight of zeolite impregnated with a heavy metal ion.

2. The article of claim 1 wherein the zeolite impregnated with a heavy metal ion is generally evenly distributed throughout the apertured plastic film.

3. The article of claim 2 wherein the topsheet comprises from about 0.5% to about 2% by weight of zeolite impregnated with a heavy metal ion.

4. The article of claim 3 wherein the metal ion is selected from the group consisting of silver, zinc, copper, and mixtures thereof.

5. The article of claim 3 wherein the zeolite is selected from the group consisting of A-type zeolite, X-type zeolite, and mixtures thereof.

6. The article of claim 5 wherein the zeolite is A-type zeolite.

7. The article of claim 1 wherein the topsheet comprises a material selected from the group consisting of apertured formed thermoplastic film, apertured hydroformed thermoplastic film, reticulated thermoplastic film, thermoplastic scrim, and mixtures thereof.

8. The article of claim 7 wherein the topsheet is apertured formed thermoplastic film.

9. The article of claim 8 wherein the topsheet comprises from about 0.05% to about 4% by weight of zeolite impregnated with a heavy metal ion.

10. The article of claim 9 wherein the topsheet comprises from about 0.5% to about 2% by weight of zeolite impregnated with a heavy metal ion.

11. The article of claim 10 wherein the metal ion is selected from the group consisting of silver, zinc, copper, and mixtures thereof.

12. The article of claim 11 wherein the zeolite is selected from the group consisting of A-type zeolite, X-type zeolite, and mixtures thereof.

13. The article of claim 12 wherein the zeolite is A-type zeolite.

14. The article of claim 1 wherein the topsheet is a resilient three-dimensional web exhibiting a fiber-like appearance and tactile impression, said web having first and second surfaces, the first surface having a multiplicity of apertures therein, each of the apertures being defined by a multiplicity of intersecting fiber-like elements interconnected to one another in the plane of the first surface, each of the fiber-like elements further exhibiting a substantially uniform U-shaped cross-section along its length, the cross-section comprising a base portion in the plane of the first surface and a side wall portion joined to each edge of the base portion, the sidewall portions extending generally in the direction of the second surface of the web, the intersecting sidewall portions being interconnected to one another intermediate the first and the second surfaces of the web, the interconnected sidewall portions terminating substantially concurrently with one another in the plane of the second surface.

15. The article of claim 14 wherein the topsheet comprises from about 0.05% to about 4% by weight of zeolite impregnated with a heavy metal ion.

16. The article of claim 15 wherein topsheet comprises from about 0.5% to about 2% by weight of zeolite impregnated with a heavy metal ion.

17. The article of claim 16 wherein the metal ion is selected from the group consisting of silver, zinc, copper, and mixtures thereof.

18. The article of claim 17 wherein the zeolite is selected from the group consisting of A-type zeolite, X-type zeolite, and mixtures thereof.

19. The article of claim 18 wherein the zeolite is A-type zeolite.

20. The article of claim 1 wherein the absorbent core additionally comprises an effective amount of an adjunct odor-controlling agent selected from the group consisting of:

a. zeolite;

b. activated carbon;

c. silica gel;

d. moisture activated encapsulated perfume;

e. cyclodextrin;

f. activated alumina; and g. mixtures thereof.

21. The article of claim 20 wherein the level of adjunct odor-controlling agent is from about 0.01 g to about 15 g per article.

22. The article of claim 21 wherein the level of adjunct odor-controlling agent is from about 0.1 g to about 10 g per article.

23. The article of claim 20 wherein the adjunct odor-controlling agent comprises a cyclodextrin/perfume complex.

24. The article of claim 20 wherein the adjunct odor controlling agent is attached to the absorbent core by a water-soluble binder.

25. The article of claim 24 wherein the water-soluble binder comprises a water soluble polymer.

* * * * *